United States Patent [19]
Schmitt et al.

[11] 4,082,722
[45] Apr. 4, 1978

[54] PRE-MIXED DENTAL COMPOSITION FOR THE PREPARATION OF A DENTAL SILICATE CEMENT

[76] Inventors: Werner Schmitt, Prinzenweg 10; Robert Purrmann, Riemerschmidstrasse 18, both of Starnberg; Peter Jochum, An der Beermahd, 8031 Hechendorf; Wolf-Dieter Zahler, Graf Toerring-Strasse 19, Hechendorf; Rainer Grimm-Lenz, Munchener Strasse 9, Seefeld, Upper Bavaria, all of Germany

[21] Appl. No.: 721,443

[22] Filed: Sep. 8, 1976

Related U.S. Application Data

[63] Continuation-in-part of Ser. No. 404,886, Oct. 10, 1973, Pat. No. 3,986,998, which is a continuation-in-part of Ser. No. 213,829, Dec. 29, 1971, abandoned.

[30] Foreign Application Priority Data

Jan. 15, 1971 Germany ............................. 2101889

[51] Int. Cl.² .............................................. C08K 3/34
[52] U.S. Cl. .................................... 260/42.43; 32/15; 106/35; 260/29.6 WB; 260/29.6 H; 260/29.6 S; 260/29.6 M; 260/42.29; 260/42.52; 260/998.11
[58] Field of Search ............ 260/998.11, 42.52, 42.43, 260/42.29, 29.6 WB, 29.6 H, 29.6 S, 29.6 M

[56] References Cited

U.S. PATENT DOCUMENTS

| | | | |
|---|---|---|---|
| 3,814,717 | 6/1974 | Wilson et al. ................. | 260/29.6 M |
| 3,882,080 | 5/1975 | Schmitt et al. ................. | 260/998.11 |

*Primary Examiner*—James H. Derrington
*Attorney, Agent, or Firm*—Ostrolenk, Faber, Gerb & Soffen

[57] ABSTRACT

Compositions, which may be mixed with water to prepare a dental silicate cement, consist essentially of a silicate glass powder and a solid polymeric material selected of polymers of unsaturated α,β-dicarboxylic acids.

5 Claims, No Drawings

PRE-MIXED DENTAL COMPOSITION FOR THE PREPARATION OF A DENTAL SILICATE CEMENT

BACKGROUND OF THE INVENTION

This is a continuation-in-part of application Ser. No. 404,886, filed Oct. 10, 1973, now U.S. Pat. No. 3,986,998 which was a continuation in part of application Ser. No. 213,829, filed Dec. 29, 1971, and now abandoned.

Silicate cements are produced, as known, by the dentist from a two component system: a mixing liquid, generally a buffered aqueous orthophosphoric acid, and as a powder component, an aluminium fluorsilicate glass (see e.g., Materials for the Practicing Dentist, p. 58-60; The C.V. Mosby Co., St. Louis, 1969).

In addition to silicate cements, amalgams and plastics are also used as permanent filling materials. The former, however, are not used for esthetic reasons where they are visible, and the plastics, though they could achieve a certain portion of the market in recent years, still meet great resistance because of the risk of discoloration. Additionally, as a rule, they are harmful to the pulpa, like the ordinary silicate cements, and can therefore only be treated by observing expensive and time-consuming precautions.

There has been no lack of attempts to improve the properties of the silicate cement (see e.g., German Offenlegungsschrift (DOS) No. 1,802,313 and 1,941,480).

A disadvantage of the silicate cements is that they are harmful to the pulpa and relatively soluble in the mouth region. The former weakness is naturally particularly serious; it necessitates the application of cavity lacquers or underfillings, procedures which are time-consuming and, in many cases, unreliable.

The object of the invention is to improve the properties, particularly the physiological compatability of the silicate cements, without reducing the other advantages, particularly their esthetic appearance and the relatively high compressive strength.

SUMMARY OF THE INVENTION

This invention relates to dental compositions for the preparation of dental cements. More particularly, this invention relates to dental compositions prepared by mixing a silicate powder with polymers of unsaturated alpha, betadicarboxylic acids.

DESCRIPTION OF THE PREFERRED EMBODIMENTS

The object of this invention is achieved by a pre-mixed dental composition for the preparation of a dental silicate cement, when mixed with water, which consists essentially of an aluminium fluorosilicate glass powder and a solid polymeric material selected from the group consisting of homopolymer of an ethylenically unsaturated alpha, beta-dicarboxylic acid of 4-5 carbon atoms, copolymer of said acids with each other, and copolymer of said acids with less than 10 mole percent of an ethylenically unsaturated monocarboxylic acid, methacrylic ester or methacrylic amide, the weight ratio of said powder to said polymer being 1.5:1 to 20:1.

Preferred are the polymers of unsaturated alpha, beta-dicarboxylic acids with 4 or 5 carbon atoms. Polymaleic acid has proved to be particularly successful, but polyitaconic acid is also suitable. Also useful are copolymers of the two above mentioned acids, as well as their copolymers with other ethylenically unsaturated carboxylic acids, particularly acrylic acid. Polymers of other carboxylic acids, for example, polyacrylic acids, can also be used as an addition to the polycarboxylic acids in an amount of about 0.1 to 50 % of said polycarboxylic acids.

The polycarboxylic acids, particularly polymaleic acid, can be easily obtained according to known methods in solid form, for example, by further concentration of concentrated solutions by freeze-drying or by precipitation from aqueous solutions with non-solvents.

The production of the polyacids used according to the invention is known (see e.g. DOS Nos. 1,944,756; 1,570,708; 1,645,100; German Pat. No. 1,162,083; J. L. Lang et al., J. of Polymer Science, A. 1, 1123(1963); C. S. Marvel et al., J. of Organic Chemistry 24, 599 (1959).

The common silicate powders can be used, that is, the inorganic glasses as they are found in commercial silicate cement powders for dental purposes in ground and sifted form in corresponding tooth-like colors (see e.g. Skinner-Phillips, The Science of Dental Materials, Fifth Edition, W.B. Saunders Co. (1960) p. 244 ff). The glasses in question can be called aluminum-fluorosilicate-glasses. They are usually produced from mixtures of aluminum-oxide and silica with the addition of fluxes like calcium fluoride or cyrolite.

After heating to about 1400° C, the glasses are ground in ball mills and sifted. By adding pigments, toothlike colors are obtained, preferably powders with different pigment additions are produced to meet all requirements.

The two solid components, that is silicate cement powder and polydicarboxylic acid, are premixed and packed as a powder mixture since the solid substances do not react with each other. The weight ratio of silicate cement powder to polymer can be 1.5:1 - 20.:1 preferably 2.3:1 - 12.5:1.

The premixed dental preparations are mixed with water to form pastes which are introduced into dental cavities as usual.

In recent years, it has become increasingly customary to sell dental preparations pre-dosed in so-called shaking caps. Liquid and powder are kept in separate compartments and combined immediately before use by suitable devices and subsequently mixed mechanically.

This pre-dosing is also applicable according to the invention.

In these systems the solid components, that is, silicate cement powder and polydicarboxylic acid, are premixed and packed pre-dosed as a powder mixture, since the solid substances do not react with each other. The second component is then water, if necessary, with the usual bacteriostatic additions, etc.

The pre-mixed dental preparation according to the invention can be produced and stored in small amounts which suffice as a pre-dosed preparation, mixed with water, for immediate use at the dentist for one patient, and it can also be produced and stored as a pre-mixed preparation of some hundred grams or more of whose bulk the dentist can take the smaller quantity which he needs, mixed with water, for the treatment of one patient.

The cements produced with the dental preparations according to the invention, unlike the known silicate cements and filling materials based on plastics, are not harmful to the pulpa. They are esthetically pleasant and thus superior to amalgams. Their solubility is favorable, that is, they are relatively insoluble under mouth conditions.

It could not be expected that the physiological properties of the silicate cements could be improved decisively by the use of polymers of unsaturated alpha, betadicarboxylic acids without losing the advantages of the silicate cements.

In the following examples, the addition of pigments customary for the production of tooth-like colors will not be mentioned specifically, since it corresponds to the state-of-the-art.

For the following examples known methods were applied to obtain polymers in solid form, e.g. by precipitating from a concentrated aqueous solution with solvents miscible with water, by drying aqueous solutions in a thin layer, preferably in the presence of drying agents, or on cylinder drying machines by applying external heat. Also, by freeze-drying from aqueous solutions, these polymers can be obtained as dry powders.

Afterwards the polymers are finely divided; during this manipulation there can be added favorably antiblocking agents in small quantities, as e.g. metal stearates, especially zinc stearate, or highly dispersed silica.

In the following examples the addition of one or more pigments and other usual additives which are customary in the production of dental cements is not specifically mentioned since it corresponds to the state of the art.

EXAMPLE 1

10 g of solid polymaleic acid are mixed with 48 g of a commercial silicate cement powder (Syntrex) and 0.2 g Aerosil (highly dispersed silica). 1.0 g of this powder mixture are spatulated with 0.26 g water. The paste is introduced in known manner into prepared tooth cavities. The set mixture has a transparency corresponding to the natural tooth.

EXAMPLE 2

A powder mixture of 10 g dry polymaleic acid, 34 g silicate cement powder (Achatit) and 0.1 g zinc stearate is made. 1.0 g of this mixture are spatulated with 0.23 g water to a paste which sets to a cement of high compressive strength.

EXAMPLE 3

The powder mixture of Example 1 is filled, in portions of each 400 mg, in the mixing chamber of two compartment containers as are described in DOS Nos. 1,910,885. Furthermore the capsules contain in the cover part 105 mg water each being stored in foil bags of plastic coated aluminum. When such a filled capsule is used, as described in DOS Nos. 1,910,885, we obtain by means of a mechanical shaking device, a cement which is used as a permanent filling material.

EXAMPLE 4

20 g polyitaconic acid are mixed with 84 g of a silicate cement powder, produced in known manner, which contains per analysis 39.5% $SiO_2$, 28.1% $Al_2O_3$, 6.1% Ca, 15.2% F, 6.6% Na and 4.0% $P_2O_5$. By adding 1 part of water to 5 parts of this powder mixture we obtain a paste which is introduced into a tooth cavity and hardens after a few minutes.

EXAMPLE 5

The following components are mixed:
10 g polymaleic acid
2.5 g polyacrylic acid
50 g silicate cement powder mentioned in Example 4
0.3 g Aerosil This powder mixture and water are spatulated in a weight ratio of 4:1.

EXAMPLE 6

10 g of a copolymer, which contains 92 mol % maleic acid and 8 mol % methacrylic acid dimethylamide, are mixed with 38 g silicate cement powder (Syntrex) and 0.2 g Cab-O-Sil (highly dispersed silica). A mixture of 0.18 g of this powder and 0.18 g water yields esthetically pleasant permanent fillings in teeth.

Instead of the polydicarboxylic acids used in the Examples, other polymers of unsaturated alpha, beta-dicarboxylic acids, as well as copolymers, can also be used. Particularly suitable are copolymers of maleic acid and itaconic acid, where the maleic acid portion can be relatively high, e.g., 80 mole %. Also suitable are copolymers of unsaturated alpha, beta-dicarboxylic acids with unsaturated monocarboxylic acids, particularly acrylic acid or methacrylic acid. Here, too, copolymers which have a relatively high content of dicarboxylic acid units deserve preference. Particularly suitable are copolymers which contain primarily maleic acid, in addition to acrylic acid or methacrylic acid, particularly copolymers which contain more than 90 mole percent maleic acid.

Suitable also are polymers or copolymers of the above mentioned type, which contain additionally small amounts, that is, not more than 10 mole percent, of monomers free of carboxyl groups. Particularly suitable are copolymers with methacrylic esters (the ester moiety can be alkyl containing preferably 1 to 4 C-atoms), acrylic amide, methacrylic amide, as well as derivatives substituted on nitrogen.

Various changes and modifications can be made in the composition of this invention without departing from the spirit and the scope thereof. The various embodiments of the invention disclosed herein serve to further illustrate the invention, but are not intended to limit it.

We claim:

1. A pre-mixed dental composition for the preparation of a dental silicate cement, when mixed with water, which consists essentially of an aluminum fluorosilicate glass powder and a solid polymeric material selected from the group consisting of homopolymer of an ethylenically unsaturated alpha, beta-dicarboxylic acid of 4–5 carbon-atoms, copolymer of said acids with each other, and copolymer of said acids with less than 10 mole percent of an ethylenically unsaturated monocarboxylic acid, methacrylic ester whose ester moiety is alkyl of 1-4 carbon atoms or methacrylic amide, the weight ratio of said powder to said polymer being 1.5:1 to 20:1.

2. The pre-mixed composition of claim 1 wherein the polymer is polymaleic acid.

3. The pre-mixed composition of claim 1 wherein the weight ratio of powder to solid polymer is 2.3:1 to 12.5:1.

4. The pre-mixed composition of claim 1, which additionally contains about 0.1 to 50 %, based on that polymeric material, of solid polyacrylic acid.

5. The pre-mixed composition of claim 1 wherein the polymer is polyitaconic acid.

* * * * *